United States Patent [19]

Wise et al.

[11] Patent Number: 4,879,472
[45] Date of Patent: Nov. 7, 1989

[54] MULTIPLEXED ELECTRONICALLY PROGRAMMABLE MULTIMODE IONIZATION DETECTOR FOR CHROMATOGRAPHY

[75] Inventors: Marcus B. Wise, Kingston; Michelle V. Buchanan, Knoxville, both of Tenn.

[73] Assignee: The United States of America as represented by the United States Department of Energy, Washington, D.C.

[21] Appl. No.: 196,693

[22] Filed: May 19, 1988

[51] Int. Cl.$^4$ ............................................ G01N 27/70
[52] U.S. Cl. .................................... 250/379; 250/382
[58] Field of Search .............. 250/379, 381, 382, 383, 250/384; 324/464, 465, 469

[56] References Cited

U.S. PATENT DOCUMENTS

| | | | |
|---|---|---|---|
| 3,154,680 | 10/1964 | Greene | 250/375 |
| 3,634,475 | 1/1972 | Lovelock et al. | 324/33 |
| 3,897,344 | 7/1975 | Marshall et al. | 250/386 |
| 4,025,794 | 5/1977 | Lovelock | 250/381 |
| 4,051,376 | 9/1977 | Lorch et al. | 250/381 |
| 4,117,332 | 9/1978 | Felton et al. | 250/374 |
| 4,137,453 | 1/1978 | Siegel | 250/382 |
| 4,538,066 | 8/1985 | Carle et al. | 250/374 |
| 4,567,368 | 1/1986 | Wells et al. | 250/383 |
| 4,705,947 | 11/1987 | Ramsey et al. | 250/384 |
| 4,721,858 | 1/1988 | Buchanan et al. | 250/379 |

OTHER PUBLICATIONS

Michell V. Buchanan, "Organic Spectroscopy," ORNL Analytical Chemistry Division Annual Progress Report for period ending Dec. 31, 1986, ORNL-6357, Apr. 1987, pp. 29-31.
A. B. Littlewood, "Gas Chromatography Principles, Techniques and Applications," Electron Capture Detectors, 2nd Ed., Academic Press, N.Y., 1970, pp. 315-322.
Michelle V. Buchanan et al., "Differentiation of Polycyclic Aromatic Hydrocarbons Using Electron Capture Negative Chemical Ionization," Organic Mass Spectrometry, vol. 19, No. 10, 1984, pp. 486-489.
R. J. Maggs, P. L. Joynes, A. J. Davies, and J. E. Lovelock, "The Electron Capture Detector-A New Mode of Operation," Anal. Chem., 43, 1966, (1971).
E. D. Pellizzari, "Electron Capture Detection in Gas Chromatography," 98, 323, (1974).
J. E. Lovelock, "Electron Absorption Detectors and Technique for Use in Quantitative and Qualitative Analysis by Gas Chromatography," Anal. Chem., 35, 474, (1963).

*Primary Examiner*—Janice A. Howell
*Assistant Examiner*—William F. Rauchholz
*Attorney, Agent, or Firm*—David E. Breeden; Stephen D. Hamel; Judson R. Hightower

[57] ABSTRACT

Method and apparatus for detecting and differentiating organic compounds based on their electron affinity. An electron capture detector cell (ECD) is operated in a plurality of multiplexed electroncially programmable operating modes to alter the detector response during a single sampling cycle to acquire multiple simultaneous chromatograms corresponding to each of the different operating modes. The cell is held at a constant subatmospheric pressure while the electron collection bias voltage applied to the cell is modulated electronically to allow acquisition of multiple chromatograms for a single sample elution from a chromatograph representing three distinctly different response modes. A system is provided which automatically controls the programmed application of bias pulses at different intervals and/or amplitudes to switch the detector from an ionization mode to the electron capture mode and various degrees therebetween to provide an improved means of tuning an ECD for multimode detection and improved specificity.

14 Claims, 6 Drawing Sheets

MULTIPLEXED ELECTRONICALLY PROGRAMMABLE MULTIMODE IONIZATION DETECTOR FOR CHROMATOGRAPHY

BACKGROUND OF THE INVENTION

This invention, which is a result of a contract with the United States Department of Energy, relates generally to ionization detection methods and devices useful in gas chromatography.

More specifically, this invention relates to methods and systems for multimode operation of ionization type detectors for use in gas chromatography.

Radiation ionization cells have been used extensively for the detection of components emerging from the effluent of a gas chromatographic column due to their broad range of sensitivity and simple rugged design. The basic design comprises a two electrode, low volume cell which houses a small quantity of a beta particle emitter such as $^3$H or $^{63}$Ni. Interaction of the beta radiation with a reagent gas, column carrier gas, and effluent generates a population of free electrons in the volume between the electrodes. Depending on the nature of the reagent and/or carrier gas used, as well as the geometry of the cell, the measured electron current will either increase (due to electron emission) or decrease (due to electron capture) as components elute from the column and enter the detector cell.

Numerous variations of this basic cell design have been disclosed, some of which have selective response and others of which are essentially universal detectors. The more important of these include the electron capture detector (ECD), the argon ionization detector, the helium ionization detector, and the cross section ionization detector. With exception of the ECD, these detectors respond by means of various reaction mechanisms which cause electron emission (increased current) as eluted components traverse the cell. The response is also effected by the manner in which the free electrons are collected to measure the current. For example, it is known in the art that the electric field applied to the cell may vary in either a continuous or pulsed fashion to increase detector stability and dynamic range.

EGD's have been used in gas chromatography as disclosed in "Gas Chromatography Principles, Techniques and Applications," Littlewood, A. B., *Electron Capture Detectors* 2nd Ed., Academic Press, N. Y., (1970), pp. 315-322. The electron capture cell contains a small quantity of $^{63}$Ni foil which emits beta particles. Under conventional operating conditions, i.e., atmospheric pressure, the beta particles collide with atoms and molecules in the gas chromatograph carrier gas, usually argon with 10% methane, resulting in a large population of free electrons formed by collisions of methane with metastable argon atoms. Ejected electrons are rapidly thermalized through collisions with neutral methane and argon. Steady state currents (standing currents) of $10^{-8}$ to $10^{-9}$ amps are produced. As components to be detected elute from the gas chromatograph column and enter the cell, they capture electrons (provided that they have a high enough electron affinity) and cause a decrease in the measured electrical current. This change in current is measured and recorded to produce a gas chromatogram.

Prior to applicants' previous invention disclosed in U.S. Pat. No. 4,721,858, issued Jan. 26, 1988, or "Variable Pressure Ionization Detector for Gas Chromatography," the subject matter of which is incorporated herein by reference thereto, this type of detector cell was operated at atmospheric pressure so that a fixed number of low energy electrons (for a given carrier gas) are available for electron capture. A threshold electron affinity is thus established, above which electrons are captured and below which electrons are not captured. This phenomenon can be used to advantage, for example, in differentiating two isomers, one of which has an electron affinity above the threshold and the other below. If both isomers are above the threshold, however, they cannot be distinguished since both components affect the measured current. In these situations it has been the practice to use negative ion chemical ionization mass spectrometry to discriminate, for example, between isomeric polycyclic aromatic hydrocarbons (PAH). The article "Differentiation of Polycyclic Aromatic Hydrocarbons Using Electron Capture Negative Chemical Ionization," Buchanan, M. V. and Olerich, G., *Org. Mass Spec.* Vol 19, No. 10, 1984 describes the use of electron capture ionization of PAH compounds to produce molecular ions, [M]−. Differentiation of isomeric PAH compounds could be effected based on relative differences in electron affinity. These experiments also indicated that the degree of discrimination was pressure dependent and increased at lower pressures.

Therefore, in accordance with the disclosure in applicants' above referenced U.S. Patent, a system and method were devised using a conventional electron capture detector operated at different pressures ranging from atmospheric to less than 1 torr to discriminate between organic compounds based on their electron affinity. Through variation of the pressure within the electron capture detector cell, the organic compounds are induced to either capture or emit electrons. Differentiation of isomeric compounds is obtained when, at a given pressure, one isomer is in the emission mode and the other in the capture mode. Further, in accordance with this pressure variation method of discrimination of organic compounds, the zero crossing pressure of a compound, defined as the pressure at which the competing electron emission and capture reactions are balanced, may be correlated to the electron affinity of a compound.

In accordance with the above, the electron capture detector has been operated essentially as a multimode ionization detector (MMID) wherein three different modes of operation are obtained by varying the pressure of the reagent gas within the detector cell. At atmospheric pressure (760 torr), the MMID responds as a conventional electron capture detector. At low pressures (1-10 torr), it responds universally like an argon ionization detector, and at intermediate pressures, the response is selective and continuously tunable as a function of pressure. This behavior is strongly related to the efficiency with which electrons and negative ions are thermally cooled within the cell which is dependent on the pressure of the gases present in the cell. In this configuration, the MMID is operated in the conventional direct current (DC) mode or the known pulsed mode for the purpose of extending the dynamic range and sensitivity, and its selectivity is altered by varying the pressure of the reagent gas within the cell.

The problem with this variable pressure detection method is that it becomes a time consuming process since the detector cell must equilibrate for several minutes at the desired operating pressure before a valid chromatogram may be obtained. Furthermore, to fully analyze a chromatographic effluent, at least three different sample injections are required in order to obtain a chromatogram of each of the three operating modes. Thus, there is a need for an ionization type detection system for gas chromatography which allows the detector to be operated in each of the three different detection modes and provide corresponding separate, simultaneous chromatograms during the period of one sample injection into the chromatograph.

SUMMARY OF THE INVENTION

In view of the above need, it is an object of this invention to provide a method and apparatus for detection and differentiation of compounds in a gaseous sample by means of an ionization type detector operated in a plurality of multiplexed response modes.

Further, it is an object of this invention to provide a method and apparatus for detection and differentiation of compounds of a single gaseous sample by means of an ionization type detector cell operated at a selected constant pressure substantially below atmospheric pressure in a plurality of multiplexed response modes to obtain a corresponding plurality of separate chromatograms simultaneously for each response mode during the sample analysis.

Yet another object of this invention is to provide a method and apparatus, as in the above objects, in which the detector is multiplexed electronically through the repeated application of controlled sequences of electrical pulses to the detector electrodes which alter the energy of the electrons participating in the chemical reactions within the detector for each of said plurality of response modes.

Other objects and many of the attendant advantages of this invention will be apparent from the following detailed description of preferred embodiments of the invention taken in conjunction with the drawings.

These objects are achieved in an apparatus for detection and differentiation of compounds by electron affinity which comprises an electron capture cell, means for injecting gaseous compounds into the cell, a pair of electrodes communicating with the cell for detection and measurement of electric current fluctuation in the cell, means for maintaining the cell at a selected constant subatmospheric pressure sufficient to allow complete free electron interaction with the injected compounds, and multiplexing means for applying controlled sequences of electrical pulses to the cell electrodes to produce a plurality of response modes within the cell so that the compounds are detected by fluctuations in cell currents produced by one of electron capture, electron emission, and a combination of electron capture and emission reactions being a function of the composition of compounds in the cell.

In accordance with another aspect of the invention, the above objects are achieved by a method for detection and differentiation of compounds based on their electron affinity, comprising the steps of injecting a gaseous mixture of compounds into an electron capture detector cell having a pair of electrodes for detection and measurement of electric current fluctuations in the cell, maintaining the pressure in the cell constant at a value substantially below atmospheric pressure, applying controlled sequences of electrical pulses to the electrodes of the cell to produce a multiplexed plurality of responses modes within the cell characterized by one of electron capture, electron emission, and a combination of electron capture and emission reactions, and detecting fluctuations in cell current separately for each mode as a function of the composition of compounds injected into the cell.

DETAILED DESCRIPTION OF THE PREFERRED EMBODIMENTS

The method and apparatus of this invention provide a means for detection and differentiation of organic compounds in an ionization type detector using programmable multimode operation of an electron capture detector to alter the response of the detector, allowing it to operate in three distinct modes. Programmed pulsing of the electrode bias voltage of the electron capture detector cell while maintaining the cell pressure at a constant subatmospheric pressure is used to alter the energy of the electrons participating in the chemical reactions within the cell. These reactions alter the cell response allowing it to operate in the three different modes of electron capture, electron emission, and a combination of both for enhanced qualitative information relating to the chemical structure of the compounds being detected in the cell during one sample injection into the cell. The multiplexed operation of the cell allows simultaneous multiple chromatograms representing the different response modes to be obtained. This feature takes advantage of the discovery that the response of a multimode ionization detector operated at a pressure in the range of from 1.10 torr can be altered simply by controlled pulsing of the electrode bias voltage which can be changed on a short time scale (milliseconds) relative to the widths of eluting chromatographic peaks (seconds). This allows considerable savings with respect to operating time, but more importantly, gives more qualitative information to the user.

Experiments with pulsed cell bias voltage detection with an electron capture detector as opposed to direct current (DC) bias voltage operation while changing the cell pressure to alter the detection mode, as in the above referenced patent, revealed that it is possible to alter the response mode electronically while maintaining a constant subatmospheric operating pressure at a level sufficient to prevent substantial cooling of free electrons available in the cell. Changes in the response were observed either by varying the voltage level of fixed width pulses at a constant frequency or by varying the time delay between fixed width pulses at a constant pulse amplitude. The application of multiplexed programed pulse sequences allows three or more chromatograms to be simultaneously collected, each representative of a different response mode for the compounds being detected. The subject process and apparatus may be implemented in stand alone or computer controlled embodiments.

Figure 1:
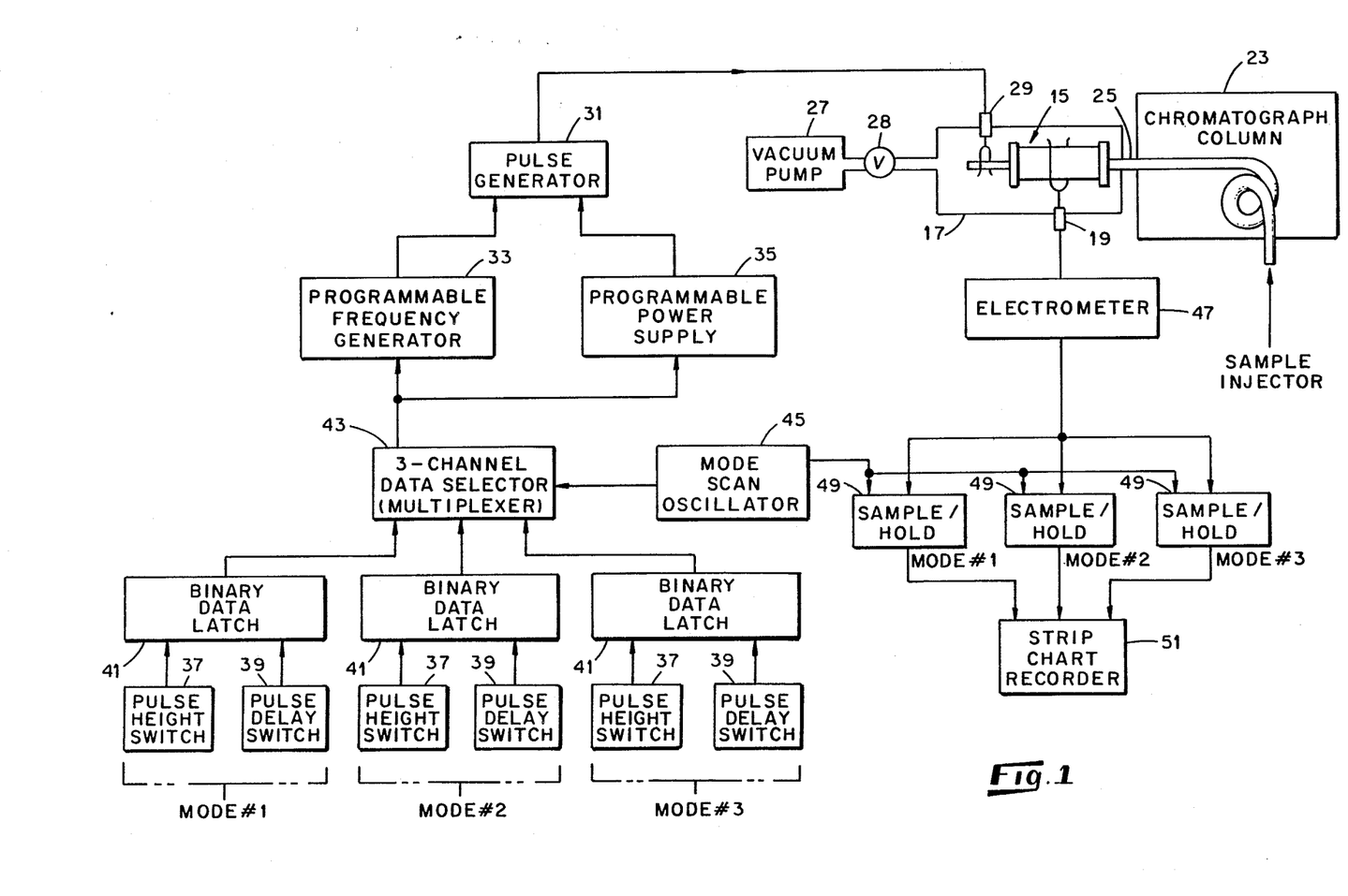
FIG. 1 is a schematic block diagram of a multiplexed electronically programmable ionization detector system according to the present invention including a manual data entry system for the programmed pulse selection.

One embodiment of the invention in the form of a hardwired three channel multiplexed multimode detector system is shown in FIG. 1. An electron capture detector (ECD) cell 15 is mounted within a vacuum tight housing 17 which is capable of supporting a high vacuum. Details of a typical ECD 15 and a vacuum housing 17 arrangement may be had by referring to the above referenced U.S. Pat. No. 4,721,858. The detector arrangement includes anode and cathode terminals 19 and 29 which provide electrical connection to the cell anode and cathode electrodes, respectively. A radioactive foil, such as nickel 63 usually in the form of an electrode coating on the anode electrode of the cell (not shown), is disposed within the cell 15 to ionize the gaseous medium within the cell by means of beta irradiation. The flow through ECD is coupled at the input end to the output of a gas chromatograph column 23 through an inlet port 25 to receive effluent from the column in a conventional manner. The outlet of the ECD exhausts into the vacuum chamber formed by the housing 17 which is held at a constant selected pressure by means of vacuum pump 27 communicating with the housing through a needle valve 28 used to regulate the pressure.

To provide the programmed pulsing of the operating voltage, or bias voltage, to the ECD, the cathode terminal 29 is connected to the output of a bias voltage pulse generator 31 which is capable of generating pulses having an amplitude of between 0 and −200 volts at frequencies from DC to 1 megahertz at pulse widths of from 1 to 10 microseconds. The pulse width is selected so that it is sufficiently long to allow for complete collection of the free electrons in the cell at the anode electrode. This is typically in the range of from about 1.5 to 2.5 microseconds and may be adjusted by a front panel control. The pulse frequency, or delay between pulses, is controlled by a programmable frequency generator 33 which produces an output signal at a frequency corresponding to the binary coded decimal (BCD) value supplied to an input thereof. The amplitude of the pulse is determined by the DC voltage level applied to an input thereof from a programmable power supply 35 which also responds to the same BCD signal at an input thereof to supply the selected voltage level to the pulse generator 31.

In this embodiment, the detector cell is designed for multiplexed operation in three different detection modes. Pulse height and pulse delay data for each of the three modes are entered by means of BCD switches 37 and 39, respectively, for each of the three channels corresponding to operating modes 1-3. These data are stored in corresponding binary data latches 41 whose outputs are connected to separate inputs of a data selector, or multiplexer, 43. The data selector 43 is a three channel multiplexer that is sequentially scanned from channel.to.channel (mode.to.mode) by a mode scan oscillator 45. The mode scan oscillator 45 is a 10 Hz oscillator coupled with a 2-Bit counter that produces scanning, or switching pulses, at 100 millisecond (msec) intervals so that each channel (mode) is repeatedly sequentially monitored for 100 msec at a time by switching the corresponding channel BCD value to the programmable frequency generator 33 and power supply 35.

The output of the ECD, taken at the anode terminal 19, is detected and amplified by an electrometer 47. The output signal from the electrometer 47, which is a voltage signal proportional to the measured detector current, is fed to three separate sample and hold amplifiers 49, one for each of the three corresponding operating channels, or operating modes. Each of the sample and hold amplifiers 49 is connected to the mode scan oscillator 45 which enables the sample and hold amplifiers 49 sequentially to sample the output of electrometer 47 only when the corresponding operating mode is selected. The outputs of the sample and hold amplifiers 49 may be recorded in various ways, such as by activating separate pens of a multiple pen chart recorder 51. In this manner three separate chromatograms, as illustrated in FIG. 3, one for each of the three operating modes are displayed on the recorder chart simultaneously as a sample is analyzed.

Figure 2:
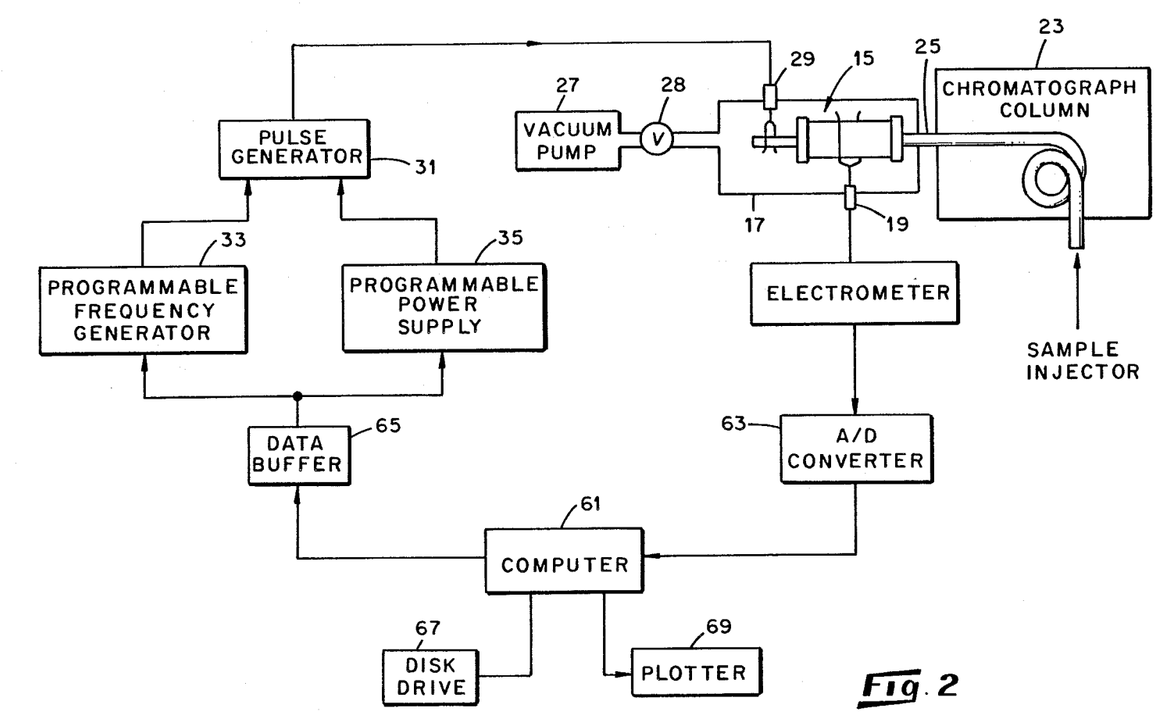
FIG. 2 is a schematic block diagram of a computer controlled multiplexed electronically programmable ionization detector system according to the present invention.

Although the system illustrated in FIG. 1 uses three different operating modes, or channels, it will be understood that the system may be designed to operate with any number of different operating modes and may best be implemented in a computer controlled arrangement as shown in FIG. 2. Referring now to FIG. 2, wherein like parts are referenced by like reference numerals to those in FIG. 1, it will be seen that a substantial portion of the electronics associated with the controlled pulse sequencing for the separate operating modes and recording of the separate mode chromatograms may be replaced with a microcomputer 61. The computer 61 may be appropriately programed to generate selected BCD data required for the selected plurality of operating modes and control the separate recording of the corresponding mode detected current values by monitoring the output of the electrometer 47 through an analog to digital converter 63. The computer 61 under program control outputs the selected BCD values for the pulse delay and pulse height to the programmable frequency generator 33 and programmable power supply 35 through a data buffer 65. These values control the pulse generator 31, as described above with reference to FIG. 1, to apply the different operating mode pulse sequences to the detector cell 15. The resulting current signal from the cell 15 at the output of the electrometer 47 is digitized by the analog converter 63. The computer 61 samples the digitized electrometer signal approximately 10 msec into each of the 100 msec pulse sequences, which allows sufficient time for the cell voltages and current to "settle" following a mode change by the applied pulse sequence. The computer scales and stores the sampled values for each mode in corresponding separate disk files of an associated disk drive 67 which are assigned to the specific operating mode to store data for each of the multiple chromatograms. The individual chromatograms may also be displayed on the computer video terminal or on a multiple pen plotter 69. Thus it will be seen that by employing computer control, the number of operating modes may be easily selected along with the appropriate pulse sequence for each mode to easily tailor the detection modes to the particular compounds being detected or differentiated.

The mechanism upon which the operation of this system is based may best be understood by first reviewing the mechanism of operating mode selection in the above referenced patent. In this system the ECD was operated with DC detection electronics, meaning that charged species generated in the detector cell are continuously accelerated to the electrodes under the influence of a continuously applied electric field. As pointed out in the referenced patent, it is also possible to apply the previously known "pulsed mode" of operation to the detector cell to extend the operating range of the detector and improve the sensitivity. However, in the previous patent, the operating detection modes within the detector cell were altered by varying the gas pressure within the cell. The operating characteristics of the detector are closely related to the efficiency with which electrons and negative ions are collisionally cooled within the cell. For example, at atmospheric pressure, a plasma containing a large number of free electrons is generated by beta ionization of the reagent gas (typically argon with 10% methane). Because of the high pressures involved, collisional cooling of the electrons is very efficient and the kinetic energy of the electrons is very low. As compounds elute from the chromatographic column, they may react with the free electrons to form negative ions which results in a decrease in the number of free electrons in the cell. The change in the number of electrons is measured with an electrometer and recorded on a suitable device to produce a chromatogram. At atmospheric pressure this behavior is analogous to conventional electron capture detection and is generally limited to the detection of compounds with positive electron affinity values.

Other operating modes are the result of pressure dependent reactions that compete with the normal electron capture process, particularly argon metastable ionization reactions. For instance, at 1 torr operating pressure and under the influence of a constant 90 volt electric field, the free electrons that are generated by beta ionization of the reagent gas are not collisionally cooled as effectively as they are at atmospheric pressure. This in turn reduces the efficiency with which compounds eluting from the chromatograph may react with the electrons. Instead, these compounds may react with a relatively large population of argon metastable atoms (that are also generated by beta irradiation) resulting in the formation of positive ions and an increase in the number of free electrons in the detector cell. Because argon metastable atoms can ionize virtually all organic compounds, this low pressure mode of operation may be considered universal. Varying results can be obtained using other nonreactive gases in the system.

Thus selective detection of compounds was achieved by operating the detector cell at pressures between the extremes at which electron capture or argon ionization dominates. At a pressure of 100 torr some compounds with sufficiently large electron affinity values will capture electrons resulting in a decrease in the number of electrons measured in the detector while compounds with low electron affinity values will still undergo argon ionization reactions more efficiently, resulting in an increase in the number of electrons measured. The pressure at which compounds begin to undergo electron capture reactions has been found to be linearly related to the electron affinity of a compound with compounds having the higher electron affinities undergoing electron capture at lower pressures. In practice this means that an operating pressure may be selected which allows compounds to be discriminated against on the basis of relative electron affinities. Since the chromatograms that are generated are the result of measuring the number of electrons in the cell, a typical chromatogram of a mixture will result in peaks that may be either positive going or negative going depending on whether electron capture or argon ionization dominates for a particular compound.

Since the response of an electron capture detector cell is found to be related to the efficiency of collisional cooling for electrons and negative ions, the different operating modes of the a detector may be achieved by operating the system at a selected continuous low pressure (1-10 torr) and using pulsed detection electronics to control the efficiency with which collisional cooling occurs. This is because collisional cooling of species in the gas phase is primarily determined by the number of collisions that occur between an energetically excited species, such as an electron or negative ion, and a low energy neutral atom or molecule, such as argon or methane. Under the application of a direct current electric field, the electrons and ions are present in the cell for a relatively constant amount of time, meaning that the number of collisions that occur are dependent primarily on the density of the reagent gas molecules within the detector cell (with the density increasing with increasing pressure).

Alternatively, it has been found that the detector cell may be operated with a constant reagent gas density (constant low pressure) and alter the amount of time that the electrons and ions are allowed to interact with the gas molecules by varying the electric field applied to the cell or varying the time that the field is applied using a detection system as described above in accordance with the present invention.

In accordance with this invention, the pressure in the detector cell is held constant at a selected pressure which is low enough to prevent substantial cooling of the free electrons and the electric field in the cell is pulsed so that the electric field is turned on only for a period of time sufficient to collect all of the free electrons at the anode electrode. During the time between detection pulses, the electric field is turned off and the electrons and ions remain within the cell where they continue to collide with the reagent gas and sample compounds. The longer the time between the applied detection pulses in a pulse sequence, the more efficient collisional cooling will be at lower pressures. This cooling time may then be controlled by the user, allowing a convenient means of altering the response of the detector.

Figure 3A:
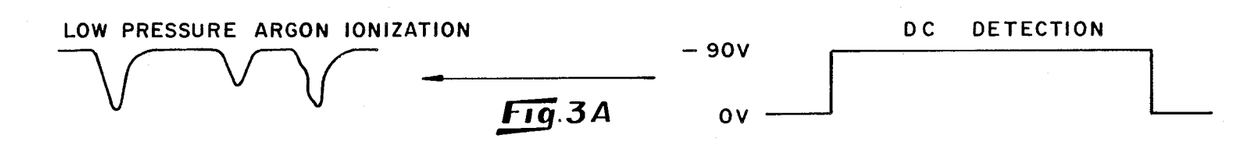
FIG. 3 is a plurality of time plots consisting of FIGS. 3A-3C which illustrate three different pulse sequences corresponding to the illustrated three different detection modes for the system of FIG. 1 and typical resulting chromatograms for the three modes.
Figure 3B:
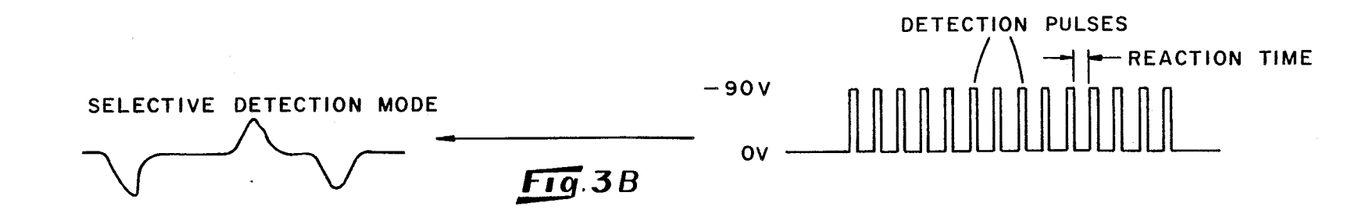
Figure 3C:
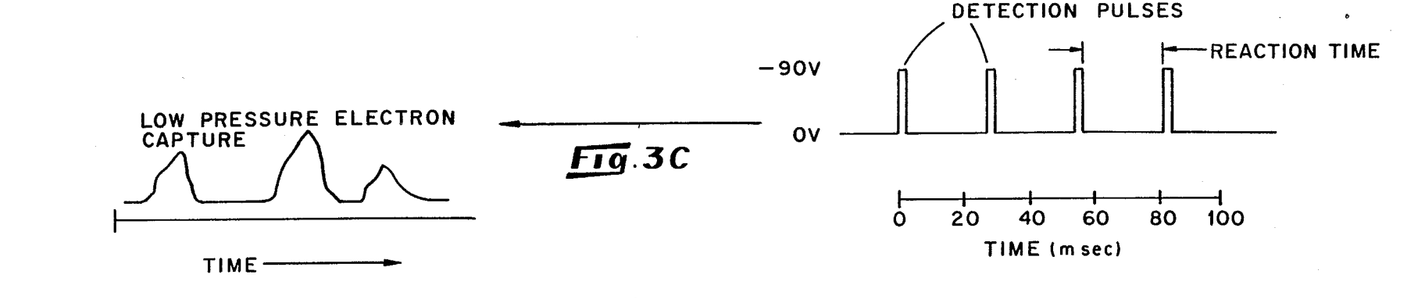

To illustrate the operation of the present system, an example of multiplexed pulsed mode operation at a constant low pressure is shown in FIG. 3, which consists of FIGS. 3A-3C corresponding to a three mode system as described above in FIG. 1. First the proper values are set in hand switches 39 for the desired multiplexing pulse sequences for the different modes as shown on the right hand side of each of FIGS. 3A-3C. Once the detector housing 17 is properly evacuated to the selected pressure in the range of between about 0.1 and 1,000 torr, the reagent gas (argon with 10% methane) is applied to the chromatographic separating column 23 and the pressure within the detector 15 is controlled at the selected level by adjusting the needle valve 28. The sample to be analyzed is injected into the column 23 and the recorder 51 is started. The pulse sequences shown are continuously sequentially applied to the detector cathode terminal 29 for periods of 100 msec duration and the sample and hold circuits 49 are updated sequentially during each corresponding pulse sequence period until the separated sample compounds eluting from the column are all detected. This detection period to provide the three separate chromatograms may take a number of seconds as indicated in the figures.

By applying a 100 msec wide pulse, which may be formed by reducing the pulse delay time to zero, at −90 volts, the detector behaves the same as that of a DC biased detector which at the lower pressure range results in argon ionization or universal detection. Because the measured number of electrons within the detector cell increases as compounds elute from the column, the peaks that appear in the chromatogram are inverted (negative) as shown in FIG. 3A. Selective detection of compounds is achieved by applying a sequence of very short (1 μsec wide) 90 volt detection pulses to the cell, as shown in FIG. 3B which has been found to be sufficient to remove all the free electrons. During the time between pulses, the free electrons produced will under go some collisional cooling. The efficiency of this cooling will be a function of length of time between the detection pulses, the selected delay time or reaction time during which reactions are allowed to take place without collection of the electrons. If the reaction time is very short, only those compounds with very high electron affinity values will undergo electron capture, while all other compounds will undergo electron emission. As shown in FIG. 3B, the first and last peaks in the example chromatogram are electron emission peaks and the middle peak is an electron capture peak corresponding to a compound with a high electron affinity. If the time between detection pulses is sufficiently long to allow all of the electrons in the detector cell to be collisionally cooled, all of the compounds eluting from the column will undergo electron capture (provided they all have a positive electron affinity value) and will appear in the appropriate chromatogram as electron capture peaks as shown in FIG. 3C. Thus, it will be seen that by adjusting the delay period electronically, the electron capture threshold for a specific compound may be easily varied. Further discussion of the nature of the reactions taking place in the cell for the various operating modes and the use of other reagent, or carrier, gases may be had by referring to the above referenced U.S. Patent.

The following examples will further illustrate the invention.

EXAMPLES

Description of Apparatus

The system used in the examples consisted of a Varian model 1200 electron capture cell which was enclosed in a stainless steel chamber. The chamber was connected to a Hoke five port valve, which was used to rapidly vary the chamber pressure between 1 torr, 760 torr, and two variable pressures. For operation at 760 torr, a port that was vented to atmosphere was selected. For operation at 1 torr, a port that was vented to a mechanical rough pump was selected. The remaining two ports permitted chamber pressure variation using Nupro precision needle valves that were connected in line with the mechanical rough pump. Chamber pressures were monitored by means of a Hastings thermocouple gauge (1–1000 millitorr) and an Omega Model PX176 pressure transducer calibrated from 0–760 torr.

A gas mixing manifold was connected to the inlet of the detector cell for the purpose of mixing reagent gases with the gas chromatograph eluent. A Nupro fine metering valve was used to control flow of the reagent gas into the system. Flow rates were monitored by means of a 0–100 ml/min variable area flowmeter.

The gas chromatograph utilized was a Hewlett Packard Model 7620A equipped with an SGE direct injector and a 25 meter X 0.25 mm (SE-52 stationary phase) fused silica capillary column. The column was fed directly into the gas mixing manifold. A vacuum seal between the column and manifold flange was made via a ⅛"×1/16" SWAGELOK ® coupling equipped with a graphite/vespel ferrule. The mixing manifold and vacuum chamber were heated with heat tape and cartridge heaters. Temperature regulation was provided by the temperature controller associated with the Hewlett-Packard 7620A GC. Both the chamber and mixing manifold were maintained at 280° C.–300° C.

The electrometer and pulsing electronics used for examples 1 and 2 was a Hewlett-Packard model 7650A associated with the Hewlett-Packard 7620A GC. The pulser was a modified to permit variation of the applied voltage between 0 and −150V, and variation of the pulse interval between 0 and 150 μsec. The pulse width was fixed at 1 μsec. Chromatograms were recorded on a Linear Instrument model 155/inch strip chard recorder.

The mounting base for the detector cell was a stainless steel 2¾" conflat flange. A 1½"×5" stainless steel conflat extension tube served as the vacuum chamber. Electrical connections to the cell were made with ¼" CAJON ® Ultra-torr "O-ring" fittings. Water cooling coils were used to minimize heat damage to the O-rings since the chamber temperature was maintained at about 300° C.

The electrical feedthroughs were specifically designed to enable rapid disassembly and reassembly of the detector system. Connections at the cell electrodes were made by spring clips. Standard BNC jacks on the high pressure side provided convenient connection to the electrometer. High temperature epoxy was used to seal the electrode, and a ceramic insert provided electrical insulation.

To improve pumping speed through the detector cell, the length of the outlet tube was reduced to 4 mm. Back diffusion of gas into the cell was generally not a problem due to the high pumping capacity of the vacuum system.

The electronics used in example 3 were designed and constructed to be functionally similar to that depicted in FIG. 1. This system may be operated in any 1 of 3 distinct modes or it may be multiplexed by continuously scanning all three modes at 100 msec intervals. Pulse widths of 1–10 μsec and pulse intervals of 1 μsec to 100 msec may be entered by means of front panel switches. The amplitude of the pulse generator may be continuously varied from 0 to −200V by means of a front panel knob. The output from the cell was multiplexed to three separate electrometers and sample/hold amplifiers. In turn, each output from the sample/hold amplifiers was connected to a different chart recorder for displaying the multiplexed chromatograms. Each electrometer is capable of responding in the range of from $10^{-12}$ to $10^{-10}$ Amp/mV.

Operating Parameters

The examples, unless otherwise stated, were performed at 300° C. Unless otherwise stated, the reagent gas used was a mixture of about 90 wt % argon with 10 wt % methane (P-10 mixture). A molecular sieve/calcium chloride drying tube was used to remove moisture from the gas.

The reagent gas flow rate was 30 ml/min. Also, due to reduced sensitivities in the argon ionization and mixed modes of operation, it was necessary to utilize an electrometer capable of responding to $10^{-13}$ amps.

EXAMPLE 1

Figure 4A:
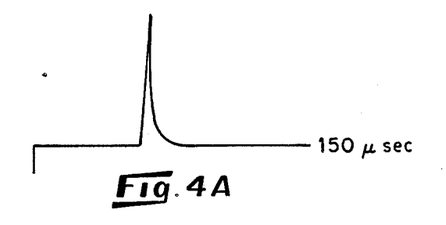
FIG. 4 is a comparison of the chromatograms (FIGS. 4A-4C) produced for benzene using the three primary pulse sequence types illustrated in FIG. 3.
Figure 4B:
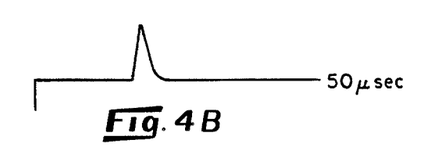
Figure 4C:
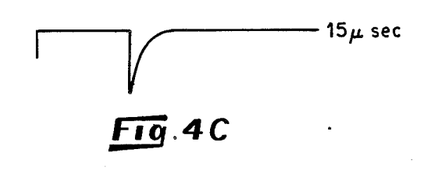

The varied response of the detector using pulsed operation according to this invention is illustrated in FIG. 4 for the detection of benzene. The response was monitored as a function of pulse interval (reaction time). When relatively long delay intervals were used (150 and 50 $\mu$sec) the reaction exhibited an electron capture response as shown in FIGS. 4A and 4B, respectively. As the pulse interval was reduced to 15 $\mu$sec, insufficient electron cooling occurred, and the benzene reaction within the cell exhibited an electron capture emission (argon ionization response) as shown in FIG. 4C by the negative going pulse in this chromatogram.

An alternative method of controlling the energy of free electrons within the detector cell is to alter the amplitude of the voltage applied to the cell while maintaining a constant low pressure. Thus, it is possible to achieve selective detection of compounds using a DC electric field and varying the voltage amplitude to provide the various detection modes. At high voltages, the electrons in the cell are accelerated to greater kinetic energies and are more likely to be captured only by compounds with high electron affinity values. At lower voltages, the kinetic energy of the electrons is much lower and collisional cooling is more effective, allowing compounds with much lower electron affinity values to undergo electron capture.

EXAMPLE 2

Figures 5A, 5D:
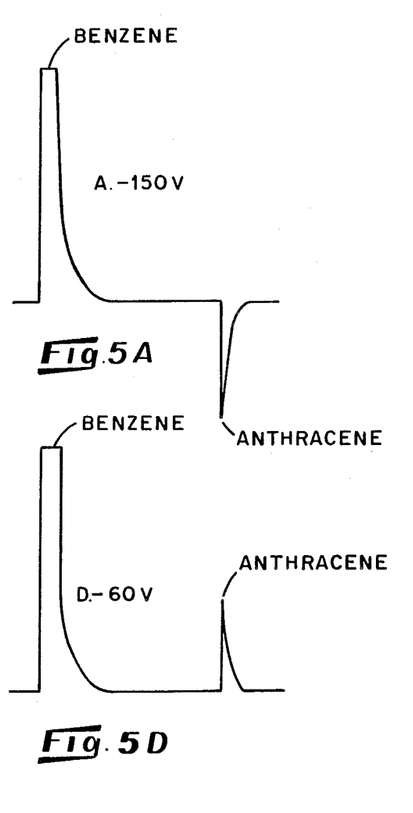
FIG. 5 is a comparison of the chromatograms (FIGS. 5A-5E) produced for anthracene in benzene at various detector operating voltages in accordance with the method of this invention.
Figure 5B:
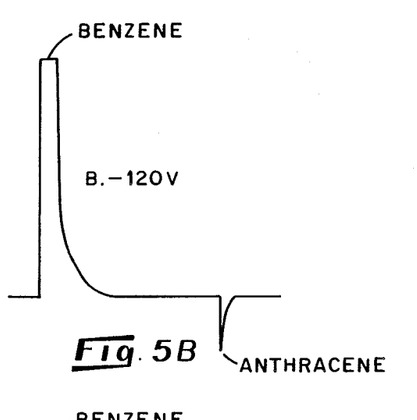
Figure 5C:
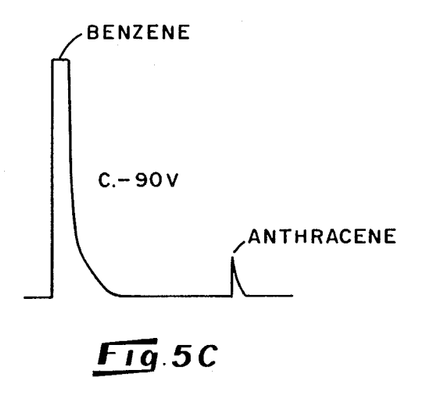
Figure 5E:
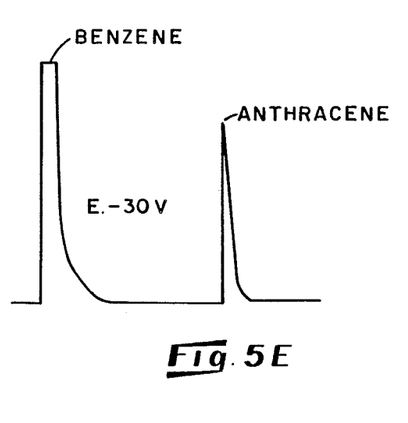

Tunable detection at low pressures using a variable voltage DC field is shown in FIGS. 5A-5E. The chromatograms show the effects of amplitude of the applied voltage on the detector response for anthracene in benzene. The chromatograms of FIGS. 5A and 5B were obtained at −150 and −120 volts, respectively. In both of these cases, the anthracene exhibited an electron emission response due to argon ionization. At these voltages, the energy of the free electrons is too high to be captured by anthracene. As the amplitude of the voltage is decreased to −90 volts, the electrons are more efficiently cooled and the anthracene peak begins to exhibit an electron capture response as shown in FIG. 5C. As the voltage is reduced to −60 volts and −30 volts, the kinetic energy of the electrons is decreased further, resulting in a larger electron capture response for anthracene, as shown in FIGS. 5D and 5E. In each of these chromatograms, the solvent peak due to the benzene exhibits an electron capture response due to its different electron affinity value. This mode of operation may be achieved in the programmable systems illustrated above by reducing the delay time to zero and varying the pulse amplitude for each mode pulse sequence to obtain the different operating detection modes.

Example 3

Figure 6A:
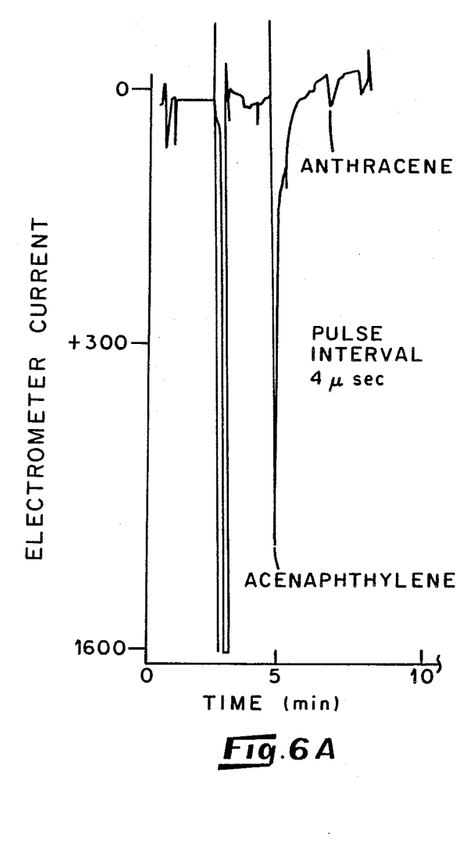
FIG. 6 is a comparison of the chromatograms (FIGS. 6A-6C) produced for differentiating acenaphthylene and anthracene using detector pulse intervals of 4, 400, and 1,225 $\mu$sec, respectively, at a constant detector cell pressure of 25 torr.
Figures 6B, 6C:
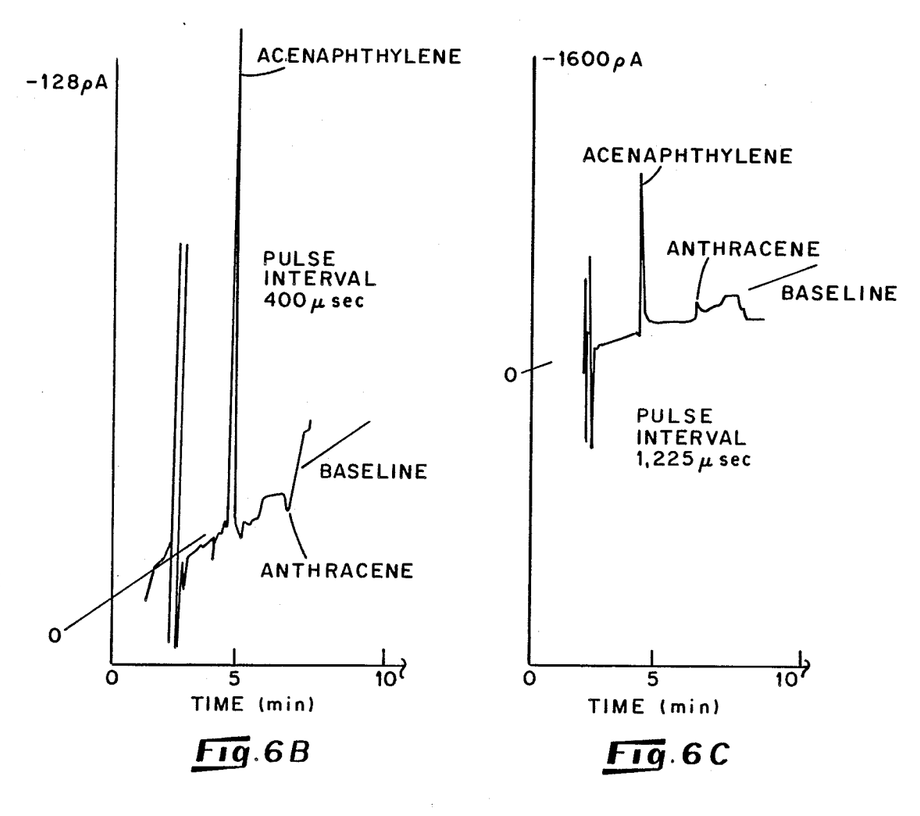

This example, the results of which are shown in FIGS. 6A-6C, illustrates the differentiation of compounds based on their electron affinity using pulsed interval variation at a constant pressure of 25 torr. Two compounds, anthracene and acenaphthylene, having different electron affinity values were injected into the chromatograph. The pressure in the cell was maintained at a constant level of 25 torr. A constant pulse with of 2 $\mu$sec was selected and the pulse amplitude was −90V. The electronics were operated in a non-multiplexed mode and sequential chromatograms were run in order to demonstrate the effects of varying the pulse interval on the response of the two compounds.

In FIG. 6A, a very short pulse interval of 4 $\mu$sec was applied to the cell in order to prevent appreciable cooling of the free electrons in the cell. Under these conditions, both acenaphthylene and anthracene exhibit electron emission as shown by the negative going peaks.

In FIG. 6B, a much longer pulse interval of 400 $\mu$sec was applied to the cell allowing for more complete electron thermalization. With these conditions, the acenaphthylene which has a higher electron affinity value (0.77 eV) then anthracene (0.49 eV) undergoes electron capture while the anthracene still exhibits electron emission.

As the pulse interval is further increased to 1,225 $\mu$sec, the free electrons in the cell are sufficiently cooled (thermalized) so that both the acenaphthylene and anthracene exhibit electron capture behavior, as shown in FIG. 6C. This example clearly demonstrates that pulse width may be varied to not only effect different response modes but also produces discrimination based on electron affinity values without having to alter the pressure in the detector cell.

Thus it will be seen that a multiplexed electronically programmable multimode ionization type detector for both chromatographic detection and differentiation of gaseous compounds has been provided in which it is possible to rapidly switch between a plurality of detection response modes during a single sample injection without varying the detector pressure or waiting for the system to equilibrate to a change in flow conditions.

We claim:

1. A device for detecting and differentiating organic compounds by electron affinity, comprising:
    an electron capture cell including a pair of electrodes communicating with said cell and an ionization radiation source disposed therein;
    means for injecting gaseous compounds into said cell;
    means for detection and measurement of electric current variation in said cell as a function of the composition of said gaseous compounds in said cell;
    means for providing a constant subatmospheric pressure within said cell; and
    means for applying programmed sequences of bias voltage pulses to said pair of electrodes of said cell at selected different intervals to alter the detection mode response of said cell.

2. A device as set forth in claim 1 wherein said means for providing a constant pressure within said cell includes a vacuum housing surrounding said cell and a vacuum source in fluid communication with the interior of said housing capable of maintaining a constant subatmospheric pressure within said housing in the range of from about 1 to 10 torr.

3. A device as set forth in claim 2 wherein said means for applying programmed sequences of bias voltage pulses includes a programmable pulse generating means for generating repeating sequences of bias voltage pulse patterns to provide multiplexed operation of said cell in a plurality of different detection modes so that said compounds are detected by one of electron capture, electron emission and a combination of electron capture and emission reactions within said cell.

4. A device as set forth in claim 3 wherein said means for detection and measurement of electric current variation in said cell includes means operatively coupled with said programmable pulse generating means for separately recording the measured current variation for each of said plurality of different detection modes in said cell as a function of the composition of said compounds introduced into said cell.

5. A device as set forth in claim 4 wherein said programmable pulse generating means includes a pulse generator connected to one of said pair of electrodes of said cell for generating selected fixed width pulses at a frequency and amplitude in accordance with programmed frequency and amplitude control signals applied to corresponding control inputs thereof; means for selectively generating separate ones of said frequency and amplitude control signals according to said plurality of different detection modes; and a sequencing means for repeatedly switching said separate ones of said control signals to said control inputs of said pulses generator.

6. A device as set forth in claim 1, wherein said means for applying programmed sequences of bias voltage pulses includes means for varying the amplitude of said sequences of bias pulses to alter the detection mode response of said cell.

7. A method for detecting and differentiating organic compounds by electron affinity, comprising the steps of:
   (a) injecting a gaseous mixture containing at least one organic compound to be detected into an apparatus for detection and differentiation of organic compounds by electron affinity comprising:
   (i) an electron capture cell including a pair of electrodes communicating with said cell and an ionization radiation source disposed therein to interact with said gaseous mixture to produce free electrons in said cell;
   (ii) means for injecting gaseous compounds into said cell;
   (iii) means for detection and measurement of electric current variation in said cell as a function of the composition of said gaseous compounds in said cell;
   (iv) means for providing a selected constant subatmospheric pressure within said cell; and
   (v) means for applying programmed sequences of bias voltage pulses to said pair of electrodes of said cell at selected different intervals to alter the detection mode response of said cell;
   (b) maintaining the pressure in said electron capture detector cell at a selected constant subatmospheric pressure sufficient to prevent total thermalization of said free electrons in said cell;
   (c) repeatedly applying a plurality of preselected electrical bias pulse sequences to said pair of electrodes of said cell to alter the detection mode of said cell between one of electron capture, electron emission and varying degrees of electron capture and emission; and
   (d) separately measuring the electric current variation in said cell for each detection mode due to one of capture and emission of electrons by said organic compound.

8. The method as set forth in claim 7, wherein said gaseous mixture contains at least two organic compounds, and wherein said method includes the step of differentiating said organic compounds based on the electrical current variations due to the capture or emission of electrons by said organic compounds.

9. The method as set forth in claim 8, wherein said gaseous mixture includes a reagent gas.

10. The method as set forth in claim 9, further including the step of introducing said gaseous mixture containing said at least two organic compounds into a gas chromatographic column prior to said injecting step.

11. The method as set forth in claim 10, wherein said gaseous mixture contains a plurality of organic compounds.

12. The method as set forth in claim 11, further including the step of separately recording the measured electric current variation for each of said detection modes in the form of a chromatogram.

13. The method as set forth in claim 12, wherein said reagent gas is a mixture of about 90 wt % argon and 10 wt % methane.

14. A method for detecting and differentiating organic compounds by electron affinity, comprising the steps of:
   a. injecting a sample of a gaseous mixture containing at least one organic compound into an electron capture detector cell having a pair of electrodes communicating with said cell;
   b. maintaining said cell at a constant pressure substantially below subatmospheric pressure;
   c. repeatedly applying sequences of a plurality of different bias voltage levels to said pair of electrodes of said cell to alter the detection mode of said cell between one of electron capture, electron emission, and varying degrees of electron capture and emission; and
   d. separatly measuring the electric current variation in said cell for each detection mode due to one of capture and emission of electrons by said compound.

* * * * *